(12) United States Patent
    Taskinen

(10) Patent No.: US 9,529,248 B2
(45) Date of Patent: Dec. 27, 2016

(54) PROTECTIVE MEANS FOR PROTECTING IMAGING MEDIA

(75) Inventor: Jari Taskinen, Tuusula (FI)

(73) Assignee: PaloDEx Group Oy, Tuusula (FI)

( * ) Notice: Subject to any disclaimer, the term of this patent is extended or adjusted under 35 U.S.C. 154(b) by 157 days.

(21) Appl. No.: 13/141,117

(22) PCT Filed: Dec. 21, 2009

(86) PCT No.: PCT/FI2009/051021
    § 371 (c)(1),
    (2), (4) Date: Jul. 18, 2011

(87) PCT Pub. No.: WO2010/072897
    PCT Pub. Date: Jul. 1, 2010

(65) Prior Publication Data
    US 2011/0299796 A1    Dec. 8, 2011

(30) Foreign Application Priority Data
    Dec. 23, 2008 (FI) .................... 20086239

(51) Int. Cl.
    *B65D 33/18*    (2006.01)
    *B65D 33/20*    (2006.01)
    (Continued)

(52) U.S. Cl.
    CPC .............. *G03C 3/003* (2013.01); *B65D 27/12* (2013.01); *B65D 27/14* (2013.01); *B65D 27/16* (2013.01);
    (Continued)

(58) Field of Classification Search
    CPC .......... A61C 2202/00; A61C 2202/01; A61C 2202/02; A61B 6/14; A61B 6/15; G03C 3/003; G03B 42/04; G03B 42/042; G03B 42/045; G03B 42/047; B65D 27/00; B65D 27/12; B65D 27/14; B65D 27/16; B65D 27/32; B65D 27/34; B65D 33/16; B65D 33/1691; B65D 33/18; B65D 33/20; B65D 75/58; B65D 75/5827; B65D 75/5833; B65D 75/5894
    (Continued)

(56) References Cited

U.S. PATENT DOCUMENTS 2,476,740 A * 7/1949 Krall ................................ 229/80
3,366,229 A * 1/1968 Sanni ............................ 206/484
(Continued)

FOREIGN PATENT DOCUMENTS

FI    92633 B    8/1994
FI    92633 C    12/1994
(Continued)

OTHER PUBLICATIONS

Finnish Search Report for priority application 20086239, dated Jun. 24, 2009.
(Continued)

*Primary Examiner* — Jes F Pascua
*Assistant Examiner* — Nina Attel
(74) *Attorney, Agent, or Firm* — Andrus Intellectual Property Law, LLP

(57) ABSTRACT

A protective means has a pouch-like structure, comprising an orifice for inserting X-ray imaging media in the protective means. In connection with the protective means there is also a closing means, which is arranged to close the orifice. Also in connection with the protective means there is a fastening means for fastening a closing means to the pouch-like structure of the protective means so that upon fastening the closing means the fastening means is arranged to be located on both sides of the orifice.

32 Claims, 3 Drawing Sheets

(51) Int. Cl.
  *G03C 3/00* (2006.01)
  *B65D 27/14* (2006.01)
  *B65D 27/16* (2006.01)
  *B65D 27/32* (2006.01)
  *B65D 27/34* (2006.01)
  *B65D 27/12* (2006.01)

(52) U.S. Cl.
  CPC ............... *B65D 27/32* (2013.01); *B65D 27/34* (2013.01); *B65D 33/18* (2013.01); *B65D 33/20* (2013.01)

(58) Field of Classification Search
  USPC .......... 383/5, 42, 66, 88, 89, 200, 210, 211, 78, 383/207–209, 205; 229/76, 80, 80.5, 81, 87.05, 229/68.1, 307–316; 206/455, 438, 439, 63.5; 378/168, 169
  See application file for complete search history.

(56) References Cited

U.S. PATENT DOCUMENTS

| | | | |
|---|---|---|---|
| 3,443,093 A * | 5/1969 | Pierson et al. | 378/169 |
| 4,033,392 A | 7/1977 | Less | |
| 4,166,538 A * | 9/1979 | Nixon et al. | 229/313 |
| 4,192,420 A * | 3/1980 | Worrell et al. | 206/205 |
| 4,510,621 A * | 4/1985 | Sak et al. | 383/89 |
| 4,709,399 A * | 11/1987 | Sanders | 383/66 |
| 5,135,313 A * | 8/1992 | Bowman | 383/5 |
| 5,150,971 A | 9/1992 | Strong et al. | |
| 5,251,755 A | 10/1993 | Kausch | |
| 5,287,960 A * | 2/1994 | Kalb et al. | 206/210 |
| 5,439,102 A * | 8/1995 | Brown et al. | 206/63.3 |
| 5,647,480 A * | 7/1997 | Insley et al. | 206/204 |
| 5,855,435 A * | 1/1999 | Chiesa | 383/204 |
| 5,902,045 A * | 5/1999 | Resteghini | 383/31 |
| 5,908,243 A * | 6/1999 | Hanning | 383/5 |
| 6,196,716 B1 * | 3/2001 | Geyer | 383/5 |
| 6,264,033 B1 * | 7/2001 | Kannabiran et al. | 206/459.1 |
| 6,270,256 B1 * | 8/2001 | Todman | 383/5 |
| 6,315,444 B1 * | 11/2001 | Koren | 378/169 |
| 2005/0036716 A1 * | 2/2005 | Geyer | 383/5 |
| 2005/0286816 A1 * | 12/2005 | Laske | 383/66 |
| 2007/0086911 A1 | 4/2007 | Yamazaki et al. | |

FOREIGN PATENT DOCUMENTS

| | | |
|---|---|---|
| FR | 1 505 539 A | 12/1967 |
| FR | 2 652 564 A1 | 4/1991 |
| GB | 1 234 694 A | 6/1971 |
| JP | S55-8924 U | 1/1980 |
| WO | 97/31293 A1 | 8/1997 |
| WO | WO 00/02782 A2 * | 1/2000 |

OTHER PUBLICATIONS

Notification of Transmittal of the International Search Report and the Written Opinion of the International Searching Authority, or the Declaration for parent application PCT/FI2009/051021, having a mailing date of Apr. 7, 2010.
Notification of Transmittal of the International Preliminary Report on Patentability for parent application PCT/FI2009/051021, having a mailing date of Dec. 3, 2010.
Finnish Office Action for priority application 20086239, dated Apr. 12, 2011.
Notification of Reason for Refusal issued in corresponding Japanese Patent Application No. 2011-542854, dispatched Nov. 14, 2013.
Notification of First Office Action issued in corresponding Chinese Patent Application No. 201310483182.8, dated Oct. 27, 2014.
Notification of Second Office Action issued in corresponding Chinese Patent Application No. 201310483182.8, dated Jul. 15, 2015.

* cited by examiner

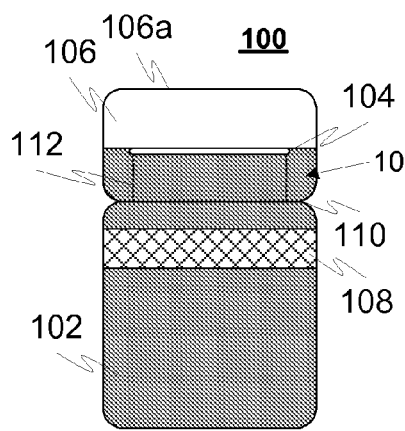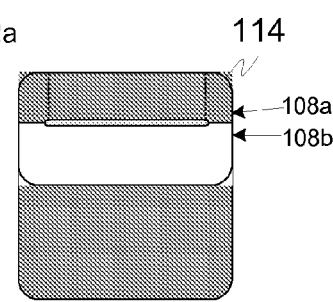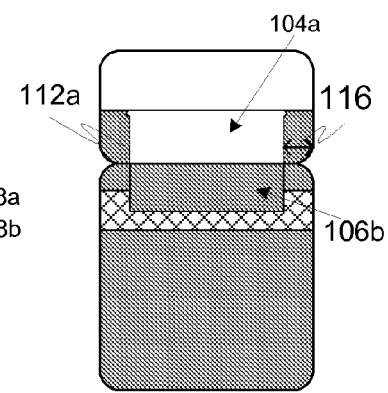
FIG. 1A  FIG. 1B  FIG. 1C
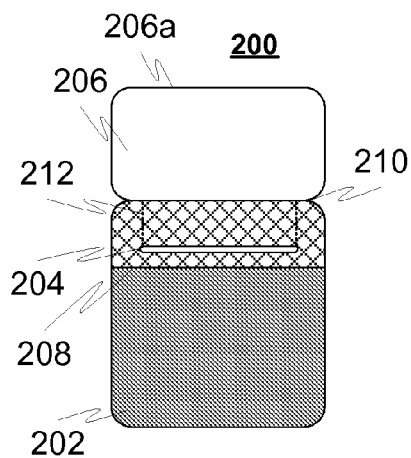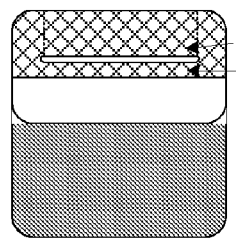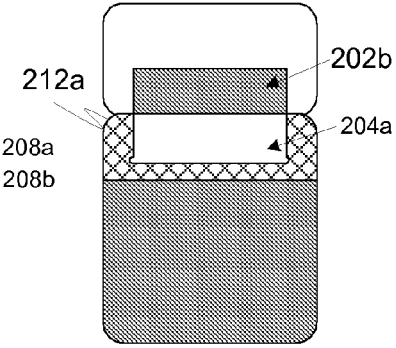
FIG. 2A  FIG. 2B  FIG. 2C
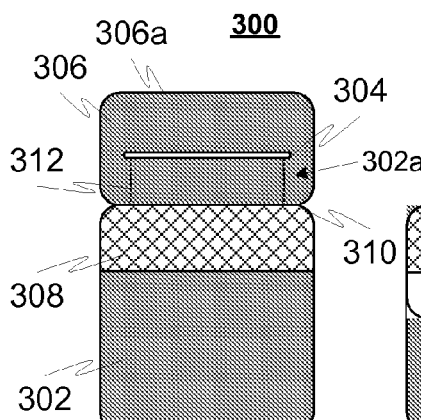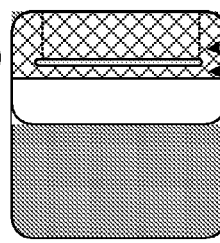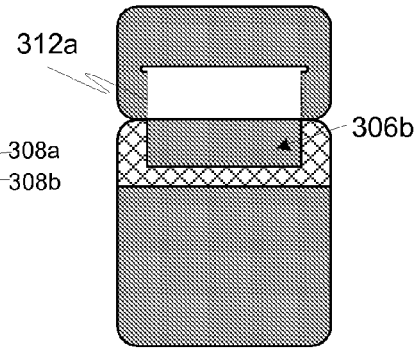
FIG. 3A  FIG. 3B  FIG. 3C

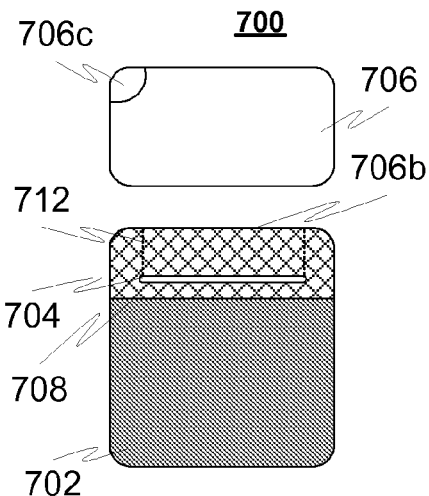
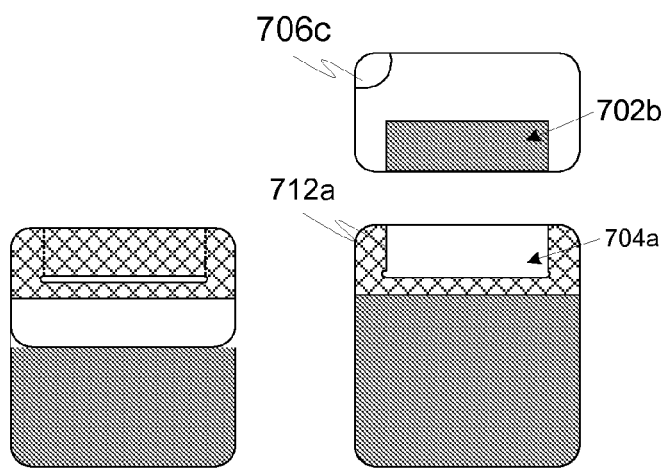
FIG. 7A        FIG. 7B        FIG. 7C
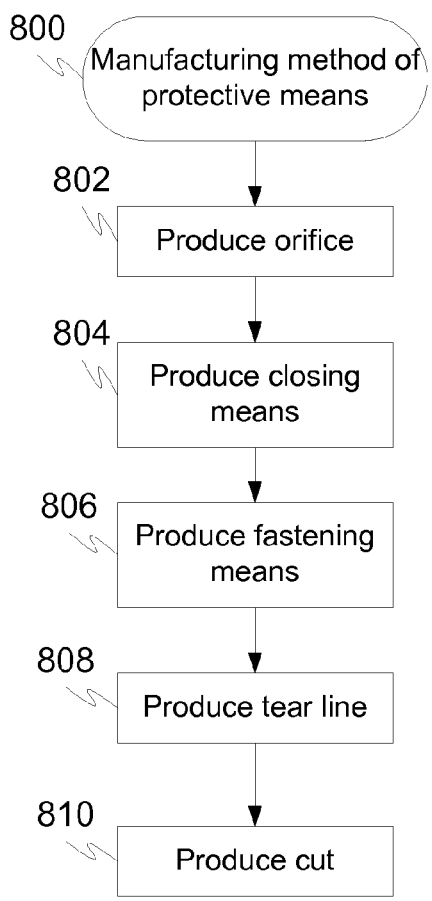
FIG. 8

PROTECTIVE MEANS FOR PROTECTING IMAGING MEDIA

CROSS-REFERENCE TO RELATED APPLICATIONS

This application is the U.S. national stage application of International Application No. PCT/FI2009/051021, filed Dec. 21, 2009, which International application was published on Jul. 1, 2010 as International Publication No. WO 2010/072897 A1 in the English language and which application is incorporated herein by reference. The International application claims priority of Finnish Patent Application No. 20086239, filed Dec. 23, 2008, which application is incorporated herein by reference.

TECHNICAL FIELD

The invention relates to the hygiene concept of imaging media such as medical imaging plates and/or sensors as well as instruments and equipment, such as imaging plate readers, used in conjunction therewith. In particular the present invention relates to a protective means for protecting an intraoral imaging plate and/or sensor, as well as a method for manufacturing a protective means.

BACKGROUND

Imaging media used in modern medical imaging comprise traditional film, reusable imaging plates, and wireless or wired X-ray sensors. If film is used, it is placed in a separate cassette protecting the film against visible fight, which cassette may become in touch with the patient and his/her secretions during the imaging process. The imaging plate, too, is shielded by a protective means during the imaging process so that an X-ray image is produced by placing the subject, such as a patient, between the X-ray source and imaging plate enveloped within the protective means. The protective means for the imaging plate may become in touch with the patient and his/her secretions during the imaging process, such as intraoral imaging, for instance, where the imaging plate protected by the protective means is inserted in the patient's mouth.

No matter which one of the above-described imaging media is used, there is the risk that pathogens originating from a patient and/or medical staff are transmitted to other patients and/or members of the medical staff via imaging media. For instance, when using imaging plates, a first risk is associated with the packaging of the imaging plate, where the imaging plate is inserted in a protective cardboard envelope which is then inserted in a protective means, such as a closable hygienic pouch, which becomes in touch with the patient, among others, during the imaging process. The imaging plate may become contaminated before insertion in the protective means for instance if a person involved in the packaging drops it onto the floor or touches it with bare hands or dirty gloves.

Another risk involves protective means, such as protective pouches, which are not completely liquid-proof so that in intraoral imaging, for example, the patient's secretions may find their way inside the protective pouch and, furthermore, contaminate the imaging plate within the protective pouch. Protective pouches which are not liquid-proof also involve the risk that potential pathogens inside the pouch may become transmitted into a patient's mouth during the imaging process.

Another risk is that a nurse, for example, takes the protective pouch from a patient's mouth and then, using the same instruments, touches elsewhere such as reader equipment or structures or even other protective pouches so that pathogens may become transmitted from the nurse to other protective means and, in the case of non-liquid-proof pouches, even onto imaging plates.

Furthermore, there is the risk that pathogens are transmitted from the imaging plate to objects in touch with the imaging plates such as conveyor mechanisms, receiving means or transfer means of the reader equipment or eject slot for the imaging plates or the trough in which imaging plates are returned from the reader equipment and, further, onto other imaging plates or persons or instruments that become in touch therewith.

Solutions are known from the prior art for improving the hygiene of intraoral imaging plates, for instance, and instruments and equipment involved in their use.

Publication FI 92633, for example, discloses a solution for protecting an intraoral image plate with two shielding bags, wherein an image plate is first inserted in an inner bag one end of which is open, and then in an outer bag, the purpose of which is to prevent the patient's saliva from ending up in the readout apparatus along with the inner bag and to protect the patient from any pathogens which may have ended up on the surface of the image plate. The image plate may be first placed inside a cardboard shield and then in an outer shielding bag, for example. Furthermore, publication U.S. Pat. No. 6,315,444 discloses a solution for protecting an imaging plate by means of an envelope, where the imaging plate is inserted in the envelope through one end of the envelope for the duration of the image-taking and removed through the other end of the envelope after the image-taking.

The solutions mentioned above involve, however, some drawbacks such as e.g. uncontrollable tearing of the shielding bag when the bag is opened. The imaging plate inside the shielding bag may then drop onto a floor or some other contaminating surface where pathogens may come into contact with the imaging plate. The envelope disclosed in U.S. Pat. No. 6,315,444 is rather complicated in its structure and manufacture since the insertion point of the imaging plate is different than the point where it is pulled out. Such a structure is considerably susceptible to leaks because it includes a plurality of apertures for the insertion and pulling-out of the imaging plate.

Furthermore, neither of the solutions mentioned above is liquid-proof because in both of them there remains a channel in the folding seam of the foldable flap, which channel allows the flow of a fluid so that a fluid can flow into the plate insertion aperture and further inside the structure and in touch with the imaging plate. Furthermore, the envelope disclosed in U.S. Pat. No. 6,315,444 will have sharp corners when the flap is folded shut. Such sharp corners are not only uncomfortable in the patient's mouth but also are a hygiene risk because a sharp corner may cut the patient's mucous membranes and thereby make it easier for pathogens to be transmitted to/from the patient's system.

Some solutions are also known for the cleaning of contaminated intraoral imaging plates. For example, publication US 2007/0086911 discloses a disinfection system where an image reading apparatus comprises a special disinfection unit which applies disinfection treatment by means of heat treatment, UV treatment, chemical treatment or gas treatment.

However, a problem with the solution disclosed in US 2007/0086911 is that the apparatus disinfects exclusively image plates inserted in the image reading apparatus. If a conventional imaging plate is disinfected through, say, UV radiation, the imaging plate must then be either erased or at least dark-treated before it can be reused, which requires time and resources because, first, there will be at least one step more in the process and, second, the imaging plate will not be readily available for reuse. Additionally, UV radiation may harm the imaging plate and shorten its useful life.

SUMMARY

An object of the invention is to eliminate disadvantages related to the prior art. According to one embodiment of the invention, the invention aims to improve the hygiene of medical imaging media such as imaging plates and associated instruments and equipment, such as imaging plate readers, and thus to minimize the spreading of pathogens between patients and/or medical staff through instruments and/or members of the staff.

Some objects of the invention are achieved through a protective means having a pouch-like structure in accordance with claim 1, and a manufacturing method in accordance with claim 14.

A protective means according to the invention is characterised in that which is expressed in claim 1 directed to a protective means.

Furthermore, a method according to the invention for manufacturing a protective means is characterised in that which is expressed in claim 14 directed to a method for manufacturing a protective means.

Some concepts used in this document have the following meanings, among others:

A "conveyor mechanism" is a mechanism which conveys or otherwise takes an imaging plate or transfer means (either with or without an imaging plate), which is inserted in a reader apparatus, for at least some distance within the reader apparatus, to be read by the read-out unit in the reader apparatus, for example. The conveyor mechanism may be a mechanism comprised of conveyor belts, mover arm, holder, rollers and/or guides. According to one embodiment, the mover arm or imaging plate holder may be the same as the gripping means used as receiving means, whereby the gripping means is arranged, in addition to receiving the imaging plate or transfer means, to transport the imaging plate or transfer means inside the reader apparatus. In some embodiments the conveyor mechanism is also adapted to transport the imaging plate or transfer means to the plate eject aperture which may be a separate eject aperture or the same as the insertion aperture, depending on the model of the reader apparatus.

"Receiver means" can be a means in conjunction with the reader apparatus for receiving an imaging plate and/or imaging plate transfer means in the reader apparatus. The receiver means may be an adapter in conjunction with the conveyor means for inserting imaging plates or imaging plate transfer means of various sizes in the reader apparatus. Activation of receiver means may comprise, for example, activation of equipment associated with the insertion aperture of the reader apparatus to enable the insertion of an imaging plate in the insertion aperture either as such or within a transfer means, such as setting the adapter in accordance with the imaging plate or transfer means. According to one embodiment, the adapter can be set in accordance with a transfer means, such as a cassette, so that the transfer means, such as a cassette, remains in the adapter and the imaging media inside the transfer means is taken from the adapter into the reader apparatus to be read, whereby it is possible to disinfect also the part of the transfer means which remains in the adapter as well as the adapter. Activation of receiver means may also comprise entry into a standby state of the gripping means in the reader apparatus, whereby an imaging plate can be placed in the gripping means either as such or within a transfer means. The receiver means may also be a port cover in the reader apparatus which opens up when activated.

A "transfer means" can be a means in which an imaging plate, which is used in intraoral imaging, for instance, is transferred from one place to another. The imaging plate may also be inserted in the reader apparatus within the transfer means to be conveyed by the conveyor mechanisms in the reader apparatus and further to be read by the reading means in the reader apparatus and further to the imaging plate eject aperture in the reader apparatus. The eject aperture may be a separate eject aperture or it may be the same as the insertion aperture. The transfer means may be an imaging plate tray, adapter or a cassette associated with the imaging media.

According to one embodiment, a protective means comprising a pouch-like structure comprises
an orifice for the insertion of imaging media in the protective means, and
a fastening means intended for fastening a closing means to the pouch-like structure of the protective means so that when fastening the closing means, the fastening means is arranged to be located on both sides of the orifice.

According to another embodiment, such a protective means comprising a pouch-like structure can be manufactured using a method in which the protective means comprising a pouch-like structure is provided with
an orifice for the insertion of imaging media in the protective means, and
a closing means in connection with the protective means, which closing means is arranged to close the orifice, and
a fastening means in connection with the protective means, intended for fastening the closing means to the pouch-like structure of the protective means so that when fastening the closing means, the fastening means is arranged to be located on both sides of the orifice.

The above-described protective means comprising a pouch-like structure has clear advantages over the prior art. The structure of the protective means is easy to manufacture, so it offers a more secure tightness than more complicated structures such as those comprising more apertures, for instance.

According to one advantageous embodiment, the fastening means is arranged such that when fastening the closing means the fastening means is adapted to be located on both sides of the orifice so that the orifice remains in between the fastening means and is closed tightly when the closing means is fastened to the fastening means on both sides of the orifice. This facilitates a completely liquid tight protective means which is easy to manufacture and can be easily and quickly closed tightly so that a patient's secretions cannot enter the protective means, especially in an embodiment including a foldable flap where it is possible that for some reason a flow channel could remain in the folding seam of the foldable flap. According to some embodiments of the invention, the fastening means, such as adhesive tape or glue, for example, is arranged to extend over to the folding seam so that there will not remain a flow channel in the folding seam.

A liquid-tight structure also makes it possible to disinfect the protective means housing an imaging plate before insertion in a patient's mouth because the disinfecting solution, for example, cannot enter the protective pouch. Thus it is ensured that staff, for example, will not be spreading pathogens in the patient's mouth, provided that the protective means is handled in a sterile manner from the point of taking it out from the disinfecting solution to the point of inserting it in the patient's mouth.

According to one embodiment, the fastening means used in the protective means may comprise adhesive tape or glue, for example. According to another embodiment, the fastening means may also be one based on heat sealing or a zipper-like structure or a groove-and-lip based fastening means. The fastening means, such as adhesive tape or glue, can be produced on both sides of the orifice already in the manufacturing process. According to one embodiment, the adhesive tape or glue may extend on both sides of the orifice up to the folding seam or even beyond. Furthermore, the adhesive tape or glue may be located in the pouch-like structure or flap-like closing means of the protective means and, further, around the orifice or, alternatively, oppositely to the orifice in the pouch-like structure or flap-like closing means of the protective means but, however, located such that upon closing, the adhesive tape or glue will be placed around the orifice, closing it.

It is also noted that the adhesive tape or glue may be protected by some means, such as thin film or strip of paper, lest the tape or glue adhere before intended, whereby the film or paper is removed just before closing.

In all embodiments, the closing means closes the orifice when being fastened to the fastening means, such as adhesive tape or glue, arranged to be located on both sides of the orifice. In order to make manufacturing simpler, it is possible to make a cut in the adhesive tape or glue at the position of the orifice already during manufacturing, for example, through which cut an imaging plate can be inserted in the protective means.

Additionally, according to one advantageous embodiment, at least one tear line can be arranged in the protective means so that when a closed protective means is opened, the protective means is torn substantially along the tear line. This brings a considerable advantage over known protective pouches, because if the fastening means comprises strong enough glue, for instance, the closing means fastened to the glue will tear uncontrollably, easily allowing secretions remaining on the outer surfaces of the protective pouch to enter the protective pouch and get in touch with the imaging plate, or even causing the imaging plate to drop from the protective pouch onto a contaminated surface.

The tear line may be realized through a pre-cut, for example, which may be arranged to become glued or otherwise tightly shut when the closing means is fastened in such a manner that it closes the orifice. In one embodiment, the tear line may be realized through perforation or other weakening. The tear line may be a straight, curved or arbitrarily shaped line along which the protective means is torn upon opening.

According to one embodiment, a folding corner in the protective means, formed when the closing means is folded around the folding seam, is rounded or, alternatively, arranged to be rounded when the protective means is closed.

Rounding can be achieved e.g. by making cuts in conjunction with the folding seam at the outer edges of the protective means.

Furthermore, according to one embodiment, at least part of the protective means or means included in it, such as closing means and fastening means, are coated with antimicrobiological material. According to one embodiment, the protective means or at least part of it may be made of antimicrobiological material. Such an antimicrobiological material may be a material belonging to Self-Assembling Monolayer End (SAME) group of materials, for example.

Further, the protective means disclosed here may be transparent at least in some part. The protective means may also be a pouch-like protective means seamed at the edges using heat sealing, for instance.

BRIEF DESCRIPTION OF THE DRAWINGS

Advantageous embodiments of the invention will be described below a little more closely, referring to the accompanying drawings in which FIG. 1 shows as an example a protective means according to the invention, FIG. 2 shows as an example a second protective means according to the invention, FIG. 3 shows as an example a third protective means according to the invention, FIG. 7 shows as an example a seventh protective means according to the invention, and FIG. 8 shows as an example a method according to the invention for manufacturing a protective means.

DETAILED DESCRIPTION OF THE DRAWINGS

Figure 4A:
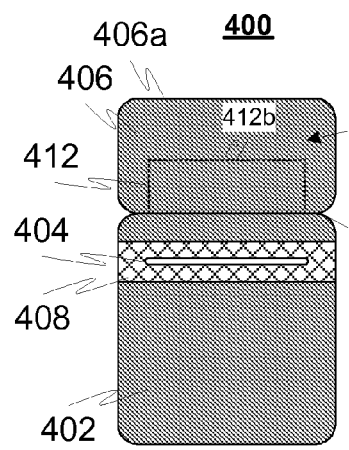
FIG. 4 shows as an example a fourth protective means according to the invention.

FIGS. 1 to 6 show, as examples, some protective means 100, 200, 300, 400, 500, 600 according to the invention comprising a pouch-like structure 102, 202, 302, 402, 502, 602, where the protective means includes an orifice 104, 204, 304, 404, 504, 604 for inserting in the protective means an imaging medium, such as an imaging plate used in intraoral imaging, for instance. In addition the protective means comprises a closing means 106, 206, 306, 406, 506, 606 arranged to be folded around a folding seam 110, 210, 310, 410, 510, 610 in such a manner as to close the orifice, and a fastening means 108, 208, 308, 408, 508, 608. The fastening means is intended for fastening the foldable part of the closing means to the pouch-like structure of the protective means so that when fastening the closing means, the fastening means is located on both sides 108a/108b, 208a/208b, 308a/308b, 408a/408b, 508a/508b of the orifice.

FIGS. 1A to 1C show, as examples, a first protective means 100 according to the invention before closing (FIG. 1A), closed (FIG. 1B), and opened after having been closed (FIG. 1C). In FIGS. 1A to 1C the pouch-like structure 102 of the protective means extends partly 102a onto the closing means 106. The pouch-like structure 102a extending onto the closing means is arranged so as to be folded around the folding seam 110 together with the closing means 106, as shown in FIG. 1B. In the protective means 100 of FIG. 1A the orifice 104 is arranged to be located in the area of the foldable closing means 106, i.e. between the free edge 106a of the closing means and the folding seam 110 formed by the closing means. Thus also the orifice 104 is folded around the folding seam 110 together with the closing means 106, as shown in FIG. 1B. Such a solution provides a better shielded and tighter protective means.

The protective means 100 also comprises a tear line 112 arranged to extend from the orifice 104 or vicinity thereof towards the folding seam 110 of the closing means (FIG. 1A, for example). When a closed protective means is opened, the closing means will substantially become torn along the tear line 112a so that an imaging plate can easily be removed through an opening 104a thus formed in the protective means without any part of the protective means that has been in contact with secretions of the patient touching the imaging plate. Furthermore, when a distance 116 (FIG. 1C) is left between the tear line and the outer edge of the protective means, it can be further ensured that the protective means will not be torn too close to a surface of the protective means, such as the outer surface, for example, which has been in contact with secretions of the patient.

When the protective means is opened, a portion 106b of the closing means which remains between the tear lines 112 is in one embodiment torn along the tear lines 112a so that the portion 106b remains fastened to the fastening means 108, as shown in FIG. 1C.

FIGS. 2A to 2C show, as examples, a second protective means 200 according to the invention before closing (FIG. 2A), closed (FIG. 2B), and opened after having been closed (FIG. 2C). In FIGS. 2A to 2C the orifice 204 is arranged to be located on the other side of the folding seam 210 formed by the closing means 206 than the free edge 206a of the closing means 206. Thus the closing means 206 is folded over the orifice 204 when the closing means 206 is fastened to the fastening means 208 (FIG. 2B). In the example depicted in FIG. 2, the fastening means 208 such as adhesive tape or glue, for instance, is arranged so as to extend over the orifice up to the folding seam 210, thus minimizing the formation of any kind of a flow channel in the vicinity of the folding seam. A similar arrangement is depicted in FIGS. 3, 5, and 6 but can be implemented also in arrangements according to other embodiments even if not depicted in the Figures.

The protective means 200 also comprises a tear line 212 arranged to extend from the orifice 204 or vicinity thereof towards the folding seam 210 of the closing means (FIG. 2A, for example). The tear line 212 may be arranged to extend at least over the fastening means 208 e.g. in an embodiment in which the fastening means does not extend up to the folding seam. The tear line 212 and fastening means may both be arranged in one embodiment to extend up to the folding seam, as shown in FIG. 2A When a closed protective means 200 is opened it will be torn substantially along the tear line 212a thus forming an opening 204a. Then, in one embodiment, a portion 202b of the pouch-like structure 202 of the protective means which remains between the tear lines 212 (including the fastening means portion which remains between the tear lines) is torn along the tear lines 212a so that the portion 202b (including the fastening means portion) remains fastened to the closing means 206 and is torn together with the closing means when the latter is opened, as shown in FIG. 2C.

FIGS. 3A to 3C show, as examples, a third protective means 300 according to the invention before closing (FIG. 3A), closed (FIG. 3B), and opened after having been closed (FIG. 3C). The protective means 300 is otherwise substantially similar to that 100 shown in FIG. 1, but in the protective means 300 the pouch-like structure 302 extends 302a onto the closing means 306 up to the free edge 306a thereof, so that the closing means 306 in its entirety can be formed of the pouch-like structure 302 of the protective means 300. In some cases this may be a simpler and faster and therefore also more advantageous way to manufacture the protective means than other embodiments.

In the embodiment depicted in FIGS. 3A to 3C the orifice 304 is arranged to be located between the free edge 306a of the closing means and the folding seam 310 formed by the closing means. Furthermore, in the embodiment depicted in FIGS. 3A to 3C the tear lines 312 are arranged to extend from the orifice 304 or vicinity thereof towards the folding seam 310 of the closing means (FIG. 3A), corresponding to the situation depicted in FIG. 1A. This way, a portion 306b which remains between the tear lines 312 is torn along the tear lines 312a so that the portion 306b remains fastened to the fastening means 308 (FIG. 3C), corresponding to the situation depicted in FIG. 1C.

Figure 4B:
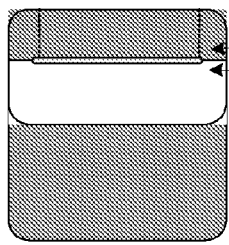
Figure 4C:
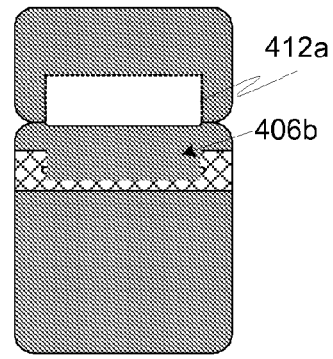

However, it is obvious to a person skilled in the art, having read this description, that the orifice 304 may also be placed elsewhere in the protective means comprising the pouch-like structure, such as at the point shown in FIGS. 2A to 2C or at the point shown in FIGS. 4A to 4C. In that case it is advantageous to arrange also the tear lines in a corresponding manner.

FIGS. 4A to 4C show, as examples, a fourth protective means 400 according to the invention before closing (FIG. 4A), closed (FIG. 4B), and opened after having been closed (FIG. 4C). In the protective means 400 the pouch-like structure 402 may extend 402a also onto the closing means 406 up to the free edge 406a thereof, so that the closing means 406 in its entirety can be formed of the pouch-like structure 402 formed by the protective means 400.

In the protective means depicted in FIGS. 4A to 4C the tear line is arranged to extend from the folding seam 410 towards the free edge 406a of the closing means (FIG. 4A). According to an embodiment, an additional tear line 412a may be arranged between the tear lines 412. In one embodiment, the additional tear line 412b may be located at such a point in the closing means that it will lie directly on top of the orifice 404 when the closing means 406 is fastened.

A portion 406b of the protective means 400 which remains between the tear lines 412 is torn along the tear lines 412a so that the portion 406b remains fastened to the fastening means 408 (FIG. 4C), corresponding to the situation depicted in FIG. 2C.

Figure 5A:
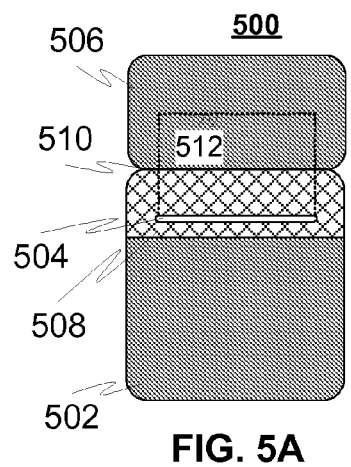
FIG. 5 shows as an example a fifth protective means according to the invention.
Figure 5B:
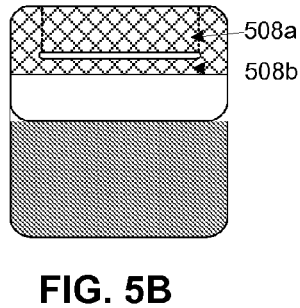
Figure 5C:
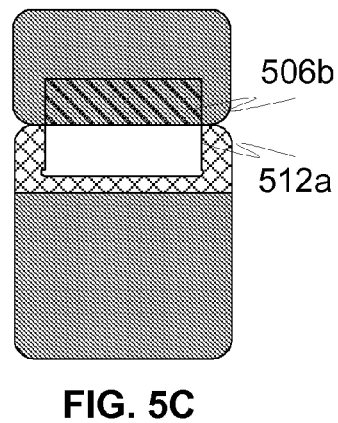
Figure 6:
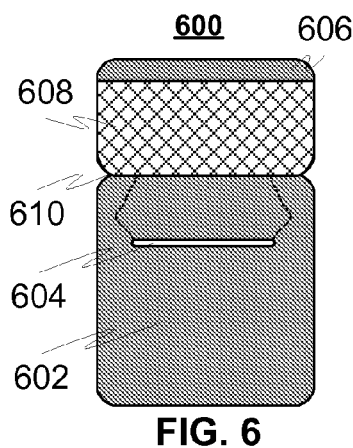
FIG. 6 shows as an example a sixth protective means according to the invention.

FIGS. 5A to 5C show, as examples, a fifth protective means 500 according to the invention before closing (FIG. 5A), closed (FIG. 5B), and opened after having been closed (FIG. 5C). To a great extent, the protective means 500 is similar to those depicted in the preceding embodiments, but in this protective means 500 the tear line 512 is arranged to extend over the folding seam onto both the pouch-like part of the protective means and the pouch-like closing means. Thus when opened the protective means 500 may open as shown in FIG. 5C, for instance, and, furthermore, the user can tear the opened part 506b further along the remaining tear line 512.

FIG. 6 shows as an example a sixth protective means according to the invention, where the tear line 612 has an arbitrary shape. It should be noted that, for clarity, the tear lines shown in FIGS. 1 to 5 are drawn straight, but the invention is by no means limited to straight tear lines but a tear line or at least part thereof may have a shape other than a straight line, such as a curve or an arbitrary shape, for instance.

FIGS. 7A to 7C show, as examples, a seventh protective means 700 according to the invention before closing (FIG. 7A), closed (FIG. 7B), and opened after having been closed (FIG. 7C). The protective means 700 further comprises a protective means 702 formed by a pouch-like structure with an orifice 704 and a tear line 712 extending from the orifice or immediate vicinity thereof towards the edge 706b of the protective means. In addition, the protective means 700 includes a closing means 706 which in this embodiment is a part which is separate from the protective means 702 having a pouch-like structure.

The closing means 706 is arranged to be placed over the orifice 704 when the closing means 706 is fastened to the fastening means 708 (FIG. 7B). Even though in FIGS. 7A to 7C the fastening means 708 is arranged to extend over the orifice up to the edge 706b, the invention is not limited to that but the fastening means 708 in another embodiment may comprise a fastening means like the one shown in FIGS. 1A to 1C and 4A to 4C where the fastening means does not extend up to the folding seam. Even though in this embodiment the fastening means 708 is drawn to be located on the protective means 702 having a pouch-like structure, in another embodiment it may also be located on the closing means 706 without departing from the fundamental idea of the invention.

When a closed protective means 700 is opened it will be torn substantially along the tear line 712a thus forming an opening 704a. Then, in one embodiment, a portion 702b of the pouch-like structure 702 of the protective means which remains between the tear lines 712 is torn along the tear lines 712a so that the portion 702b remains fastened to the closing means 706 and is torn together with the closing means when the latter is opened, as shown in FIG. 7C. In one embodiment the portion 702b and closing means may remain attached to the edge 706b, whereby the protective means, when opened, looks similar to the opened protective means shown in FIG. 2C, for example.

FIG. 8 shows as an example a method 800 according to the invention for manufacturing a protective means, which method comprises a step 802 for producing an orifice in the protective means having a pouch-like structure, a step 804 for producing a closing means such that the closing means will close the orifice, and step 806 for producing a fastening means for fastening the closing means to the pouch-like structure of the protective means so that upon fastening the closing means, the fastening means is located on both sides of the orifice.

Step 806 may also include the placement of the fastening means on both sides of the orifice and possibly also the making of the cut in the fastening means at the position of the orifice, when the fastening means comprises adhesive tape or glue.

In the method 800, the pouch-like structure may be made to extend at least partly onto the closing means and also arranged so as to be folded together with the closing means. In step 802, the orifice may in one embodiment be located in the area between the folding seam and the free edge of the closing means or, alternatively, on the other side of the folding seam than the free edge of the closing means.

The method may also comprise a step 808 for producing a break line in the protective means, such as one of those described above, using a pre-cut, perforation and/or weakening, for example. Furthermore, the method may also comprise a step 810 for making a cut in conjunction with the folding seams of the protective means depicted in FIGS. 1 to 6 so that when the protective means is closed, the folding corner becomes rounded 114, as shown in FIG. 1B, for instance.

Only a few embodiments of the solution according to the invention were described above. The principle according to the invention, as regards e.g. implementation details and field of application, may naturally be modified within the scope of the invention defined by the claims. Especially it should be noted that in cases depicted in FIGS. 1A to 1C and 3A to 3C, for example, the fastening means, such as adhesive tape or glue, can be located around the orifice 104, 304 in the closing means 106, 306 without changing the general idea of the protective means described here. It should also be noted that the adhesive tape or glue may in other embodiments, too, be located in the flap-like closing means 206, 406, 506 in the manner described in FIG. 6, for instance. Further, it should be noted that the tape or glue may in any embodiment extend up to the folding seam, as shown in the examples of FIGS. 2, 3, 5, and 6.

Also it should be noted that the closing means, particularly closing means 706, may in itself comprise a fastening means. According to one embodiment, the closing means, particularly closing means 706, may be entirely comprised of adhesive tape, such as one-sided tape, so that no other fastening means are necessarily needed. When the closing means, such as closing means 706, is entirely comprised of adhesive tape, for example, it is advantageous to leave in the closing means a portion, such as portion 706c, which is substantially made of a non-fastening material and thus will not be fastened to the pouch-like part of the protective means so that, when opening the protective means, the closing means can be torn open at portion 706c. A similar portion 706c may also be included in the closing means depicted in the other Figures even though not shown therein.

The invention claimed is:

1. An intraoral protective apparatus for protecting imaging media during medical imaging comprising:
 a pouch-like structure configured to contain imaging media in a liquid-tight manner;
 a first opening through the pouch-like structure and configured to receive the imaging media as the imaging media is inserted into the pouch-like structure, the pouch-like structure sized to be inserted into a patient's mouth while containing the imaging media;
 a closing structure comprising a foldable flap connected to the pouch-like structure at a folding seam and configured to close about the folding seam to close the first opening after the imaging media has been inserted into the pouch-like structure;
 at least one tear line in the pouch-like structure, the at least one tear line extends from the opening in the direction of the folding seam; and
 a fastener configured to fasten the closing structure onto the pouch-like structure with respect to the first opening wherein when the first opening is closed the fastener and closing structure are located on all sides of the first opening and extends to the folding seam to surround the at least one tear line so that the first opening and the at least one tear line are closed in a liquid-tight manner so as to protect the imaging media from liquids;
 wherein unfastening of the closing structure from the pouch-like structure opens a second opening along the at least one tear line and the first opening into the pouch-like structure and wherein the second opening is configured to allow for removal of the imaging media from the pouch-like structure.

2. The apparatus according to claim 1, wherein the fastener comprises an adhesive.

3. The apparatus according to claim 2, further comprising a releasable cover on the adhesive, wherein the releasable cover prevents the fastener from fastening the closing structure to the pouch-like structure.

4. The apparatus according to claim 3, wherein the releasable cover is selected from a group consisting of film and paper.

5. The apparatus according to claim 1, wherein the folding seam has at least one rounded folding corner.

6. The apparatus according to claim 1, wherein the at least one tear line extends through the pouch-like structure.

7. The apparatus according to claim 1, wherein the at least one tear line is defined by perforations.

8. The apparatus according to claim 1, wherein the at least one tear line is defined by a weakening in the pouch-like structure.

9. The apparatus according to claim 1, wherein the at least one tear line is straight linear.

10. The apparatus according to claim 1, wherein the at least one tear line is not straight linear.

11. The apparatus according to claim 1, wherein the at least one tear line extends from the folding seam to the first opening so that the first opening and second opening are connected, and the second opening is larger than the first opening.

12. The apparatus according to claim 11, wherein the first opening and second opening are formed in the pouch-like structure and the pouch-like structure and the foldable flap at least partially overlap.

13. The apparatus according to claim 11, wherein the pouch-like structure extends across the foldable flap and the closing structure comprises a portion of the pouch-like structure, first opening and second opening are formed in the foldable flap, the first opening and second opening connected to an interior of the pouch-like structure through an interior of the closing structure.

14. The apparatus according to claim 1, wherein the pouch-like structure extends across the foldable flap and the closing structure comprises a portion of the pouch-like structure, the first opening is formed in the pouch-like structure and the closing structure, the second opening is formed in the pouch-like structure and the closing structure, and the first opening and the second opening are connected to an interior of the pouch-like structure.

15. The apparatus according to claim 1, wherein the apparatus comprises an antimicrobial surface or is made of antimicrobial material.

16. A method for using an apparatus for protecting imaging media for intraoral imaging media in dental imaging, said imaging media being readable when inserted in a reader apparatus, the method comprising:
   providing an apparatus comprising:
      a pouch-like structure configured to contain imaging media in a liquid-tight manner;
      a first opening through the pouch-like structure, the first opening configured to receive the imaging media as the imaging media is inserted into the pouch-like structure;
      a closing structure comprising a foldable flap connected to a pouch-like structure at a folding seam and configured to close the first opening after the imaging media has been inserted into the pouch-like structure; and
      at least one tear line in the pouch-like structure from the first opening to the folding seam;
      a fastener configured to fasten the closing structure onto the pouch-like structure to surround the first opening and the at least one tear line so that the apparatus is closed in the liquid-tight manner so as to protect the imaging media from liquids;
   placing the imaging media in the pouch-like structure;
   closing the first opening with the closing structure folded about the folding seam such that the fastener is located on all sides of the first opening so as to protect the imaging media from liquids, the pouch-like structure sized to be inserted into a patient's mouth while containing the imaging media;
   inserting the apparatus in a patient's mouth;
   exposing the imaging media to x-rays;
   removing the apparatus from the patient's mouth;
   opening the apparatus by at least partially removing the closing structure from the pouch-like structure to open a second opening in the pouch-like structure by tearing along the at lest one tear line in a direction of the folding seam;
   removing the imaging media from the apparatus through the second opening.

17. The method of claim 16, further comprising:
   disinfecting the pouch-like structure in a liquid disinfectant after closing the first opening and prior to inserting the apparatus in the patient's mouth.

18. The method of claim 17, further comprising:
   fastening the closing structure onto the pouch-like structure.

19. The method of claim 16, further comprising:
   placing the imaging media in a transfer means;
   wherein placing the imaging media in the pouch-like structure further comprises placing the transfer means in the pouch-like structure.

20. The method of claim 19, wherein inserting the apparatus in the patient's mouth further comprises placing the transfer means in the patient's mouth, and removing the apparatus from the patient's mouth further comprises removing the transfer means from the patient's mouth.

21. The method of claim 19, further comprising:
   disinfecting the pouch-like structure in a liquid disinfectant after closing the first opening and prior to inserting the apparatus in the patient's mouth.

22. An intraoral protective apparatus for protecting imaging media during medical imaging, the apparatus comprising:
   a pouch-like structure configured to contain imaging media in a liquid-tight manner, the pouch-like structure sized to be inserted into a patient's mouth while containing the imaging media, the pouch-like structure comprising; a foldable flap and a folding seam and configured to be folded about the folding seam to contain the imaging media in a liquid-tight manner within the pouch-like structure;
   a first opening through the pouch-like structure, the first opening spaced apart from the folding seam and configured to receive the imaging media as the imaging media is inserted into the pouch-like structure, the foldable flap configured to fold about the folding seam to close the first opening;
   at least one tear line located interior of any free edge of the pouch-like structure and extending from the first opening to the folding seam; and
   a fastener on the pouch-like structure that fastener surrounds the first opening, extends to the folding seam, and surrounds the at least one tear line, the fastener secures the foldable flap to the pouch-like structure across the first opening and the at least one tear line, so that the pouch-like structure is closed in the liquid-tight manner so as to protect the imaging media from liquids; wherein the apparatus is configured such that unfastening of the foldable flap from the pouch-like structure opens a second opening along the at least one tear line the second opening comprises the first opening, and wherein the second opening is configured to allow for removal of the imaging media from the pouch-like structure.

23. The apparatus according to claim 22, wherein the foldable flap is connected to the pouch-like structure in an at least partially overlapping configuration, and the pouch-like structure is configured to be folded about the folding seam.

24. The apparatus according to claim 23, wherein a portion of the foldable flap that is defined by the tear line is configured to remain fastened to the pouch-like structure when the foldable flap is unfastened from the pouch-like structure.

25. The apparatus according to claim 23, wherein the first opening and second opening are formed in the foldable flap.

26. The apparatus according to claim 25, wherein the first opening and the second opening are connected to an interior of the pouch-like structure through an interior of the foldable flap.

27. The apparatus according to claim 22, wherein a portion of the pouch-like structure that is defined by the at least one tear line is configured to remain fastened to the foldable flap when the foldable flap is unfastened from the pouch-like structure.

28. The apparatus according to claim 22, wherein the apparatus comprises an antimicrobial surface or is made of antimicrobial material.

29. A method for manufacturing an intraoral protective apparatus for protecting imaging media during medical imaging, the method comprising:
    forming an apparatus comprising a pouch-like structure configured to contain imaging media in a liquid-tight manner, the pouch-like structure adapted and sized to be inserted into a patient's mouth while containing the imaging media;
    forming a first opening through the pouch-like structure, the first opening configured to receive the imaging media as the imaging media is inserted into the pouch-like structure;
    providing a closing structure connected to the pouch-like structure and configured to be folded about a folding seam, the closing structure configured to close the first opening after the imaging media has been inserted into the pouch-like structure;
    providing a fastener configured to fasten the closing structure onto the pouch-like structure, wherein when the closing structure is folded, the fastener surrounds the first opening and extends to the folding seam so that the apparatus is closed in the liquid-tight manner so as to protect the imaging media from liquids; and
    providing at least one tear line in the pouch-like structure, the at least one tear line extends from the first opening in the direction of the folding seam and the at least one tear line is surrounded by the fastener and the closing structure when the closing structure is folded, the at least one tear line configured to tear upon unfastening of at least a first portion of the closing structure from the pouch-like structure to form a second opening extending from the first opening in the pouch-like structure, the second opening larger than the first opening to facilitate removal of the imaging media from the pouch-like structure.

30. The method according to claim 29, wherein the fastener surrounds the at least one tear line so that the apparatus is closed in the liquid tight manner.

31. The method according to claim 29, wherein the closing structure is connected to the pouch-like structure in an at least partially overlapping configuration, and the pouch-like structure is configured to be folded about the folding seam.

32. The method according to claim 29, wherein at least a second portion of the closing structure remains fastened to the pouch-like structure when the first portion of the closing structure is unfastened from the pouch-like structure.

* * * * *